(12) United States Patent
Jau et al.

(10) Patent No.: US 7,598,376 B2
(45) Date of Patent: Oct. 6, 2009

(54) PROCESS FOR THE PREPARATION OF [1,4,5]-OXADIAZEPINE DERIVATIVES

(75) Inventors: Beat Jau, Muenchwilen (CH); Marian Parak, Muenchwilen (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 150 days.

(21) Appl. No.: 10/498,865

(22) PCT Filed: Dec. 17, 2002

(86) PCT No.: PCT/EP02/14414

§ 371 (c)(1),
(2), (4) Date: Mar. 14, 2005

(87) PCT Pub. No.: WO03/051853

PCT Pub. Date: Jun. 26, 2003

(65) Prior Publication Data

US 2005/0159313 A1   Jul. 21, 2005

(30) Foreign Application Priority Data

Dec. 18, 2001 (CH) .................................. 2313/01

(51) Int. Cl.
*C07D 285/36* (2006.01)
*C07D 498/04* (2006.01)
*A01N 25/00* (2006.01)

(52) U.S. Cl. ...................................... 540/545; 504/218
(58) Field of Classification Search ................ 540/484, 540/485, 486, 545; 504/218
See application file for complete search history.

(56) References Cited

U.S. PATENT DOCUMENTS 5,015,637 A * 5/1991 Effland et al. .......... 514/211.08
2009/0124800 A1* 5/2009 Faber et al. ................. 540/545

FOREIGN PATENT DOCUMENTS

WO          0117973         3/2001

OTHER PUBLICATIONS

Kotelko, Barbara et al., AN 103:142028 CASREACT, Hexahydro-1,4,7-oxadiazepine derivatives, abstract of PL 123646. (Nov. 30, 1982).*
Kotelko, B. et al. AN 103:142027 CASREACT, abstract of PL 123647.*
Krakowiak et al. AN 97:198176 CASREACT, Acta Ploniae Pharmaceutica (1981), 38(6), 673-8.*

* cited by examiner

*Primary Examiner*—Sabiha Qazi
(74) *Attorney, Agent, or Firm*—James Cueva

(57) ABSTRACT

A process for the preparation of [1,4,5]-oxadiazepine derivatives by reaction of N,N'-diacyl-hydrazines with 2,2'-disubstituted diethyl ethers to form 4,5-diacyl-[1,4,5]-oxadiazepines and reaction of the latter compounds with a hydrohalic acid.

14 Claims, No Drawings

PROCESS FOR THE PREPARATION OF [1,4,5]-OXADIAZEPINE DERIVATIVES

The present invention relates to a novel process for the preparation of [1,4,5]-oxadiazepines and to their use as intermediates in the preparation of herbicides of the tetrahydropyrazolodione type.

According to PL 123646 and SU 784 264, [1,4,5]-oxadiazepines are prepared by reacting various N,N'-diacylated hydrazines with 2,2'-dichlorodiethyl ether in DMFA as solvent.

It has now been found, surprisingly, that the preparation of [1,4,5]-oxadiazepine derivatives can be significantly improved in respect of yield and purity when the reaction of N,N'-diacyl-hydrazines to form the corresponding 4,5-diacyl-[1,4,5]-oxadiazepines and the further reaction thereof to form the [1,4,5]-oxadiazepines are carried out in certain organic, polar solvents.

The present invention accordingly relates to a process for the preparation of [1,4,5]-oxadiazepine derivatives by (1) reaction of a N,N'-diacylhydrazine with a 2,2'-disubstituted diethyl ether in a polar solvent in the presence of a base and at elevated temperature to form the corresponding 4,5-diacyl-[1,4,5]-oxadiazepine and (2) optionally reaction of the latter compound with a hydrohalic acid in a polar solvent to form the corresponding [1,4,5]-oxadiazepine at elevated temperature, wherein in reaction step (1) a solvent selected from the group DMSO, sulfolane, NMP and DMA is used and in reaction step (2) a high-boiling polar solvent is used.

Preferred N,N'-diacylhydrazines correspond to formula I $R_1$—CO—NH—NH—CO—$R_2$ (I), wherein $R_1$ and $R_2$ each independently of the other are hydrogen, $C_1$-$C_5$alkyl, $C_1$-$C_5$haloalkyl, $C_2$-$C_5$alkenyl, $C_2$-$C_5$alkynyl, phenyl, alkylphenyl, halophenyl, alkoxyphenyl, benzyl, alkylbenzyl, halobenzyl or alkoxybenzyl, or $R_1$ and $R_2$ together are $C_1$-$C_4$alkylene, 1,2-phenylene or 1,8-naphthylene.

Preferred 2,2'-disubstituted diethyl ethers correspond to formula II $R_3$—$CH_2CHR_5$—O—$CHR_6CH_2$—$R_4$ (II), wherein $R_3$ and $R_4$ each independently of the other are halogen or a radical of formula —$OS(O)_2R_7$, wherein $R_7$ is $C_1$-$C_5$alkyl, $C_1$-$C_5$haloalkyl, phenyl, alkylphenyl or halophenyl, and $R_5$ and $R_6$ each independently of the other are hydrogen, $C_1$-$C_5$alkyl, $C_2$-$C_5$alkoxyalkyl, phenyl, alkylphenyl, alkoxyphenyl or halophenyl.

Bases suitable for use in reaction step (1) are especially hydroxides and carbonates and alcoholates of alkali and alkaline earth metals, especially potassium hydroxide and potassium carbonate, and mixtures of such bases, especially of potassium hydroxide and potassium carbonate.

Hydrohalic acids are preferably hydrogen chloride and hydrogen bromide.

Solvents for use in reaction step (1) include DMSO [$(CH_3)_2SO$], sulfolane [$(CH_2)_4SO_2$], NMP [$(CH_2)_3CONCH_3$] and DMA [$CH_3CON(CH_3)_2$] and mixtures thereof, preference being given to NMP and especially DMSO. In reaction step (2) there are preferably used alcohols having a boiling point above 100° C., for example n-butanol, n-pentanol, cyclohexanol, phenol, benzyl alcohol and especially glycol, diethylene glycol, glycerol and $C_1$-$C_4$alkoxy-$C_1$-$C_4$alcohols, such as methoxyisopropanol and ethoxyethanol.

The alkyl radicals appearing in the substituent definitions of compounds of formulae I and II contain from 1 to 5 carbon atoms and are, for example, methyl, ethyl, propyl, butyl or pentyl and also branched isomers thereof. Alkoxy radicals are derived from the mentioned alkyl radicals. Alkenyl and alkynyl radicals each have from 2 to 5 carbon atoms and are, for example, ethenyl, propenyl, ethynyl and propynyl and branched isomers thereof, and also butenyl, butynyl, pentenyl, pentynyl and branched and di-unsaturated isomers thereof. The phenyl radicals may be further substituted by alkyl or alkoxy, for example each having from 1 to 4 carbon atoms, which preferably occupy the ortho- or meta- or ortho- and para-position(s). Halogen is preferably fluorine, chlorine or bromine.

The term "elevated temperature" denotes especially a temperature range of from 30 to 150° C. It is especially advantageous to proceed in a range of from 60 to 100° C. in reaction step (1) and in a range of from 30 to 60° C. in reaction step (2).

The N,N'-diacylhydrazines used according to the invention as starting materials are known and can be obtained in a manner known per se, e.g. as described in PL 123646 B1.

In reaction step (1) it is preferable to use from 1.5 to 4 equivalents of the 2,2'-disubstituted diethyl ether, based on N,N-diacylhydrazine.

The 4,5-diacyl-[1,4,5]-oxadiazepines obtained in this reaction step can be obtained especially by precipitation from alcohols such as methanol, ethanol, propanol, isopropanol, methoxyisopropanol and ethoxyethanol. They are generally obtained in yields of from 40 to 76% and in a purity of more than 95%. It is not necessary, however, to isolate those intermediates; they can be introduced directly into the next step by replacing the solvent of reaction step (1) by the solvent of reaction step (2).

It may be possible further to improve reaction step (1) in terms of yields by the addition of potassium iodide, a crown ether, e.g. 18-crown-6, and a phase transfer catalyst, e.g. benzyltriethylammonium chloride, TBAB' and Aliquats.

The hydrohalic acids required for the removal of the acyl (protecting) groups in reaction step (2) can be added directly by passing them into the reaction mixture. They can, however, also be produced in situ, for example by utilising the reaction of acid halides, such as acetyl chloride, with the alcohols present as solvent. Preferably from 2 to 5 equivalents of hydrohalic acid, based on 4,5-diacyl-[1,4,5]-oxadiazepine, are used.

The yields of isolated [1,4,5]-oxadiazepine salts are generally from 80 to 95% and, over both reaction steps, from 60 to 70%. The purity of the salts is usually about 90%.

The synthesis of the [1,4,5]-oxadiazepine derivatives is usually carried out by introducing the N,N'-diacylhydrazine into the polar solvent and then adding an excess of base. The 2,2'-di-substituted diethyl ether, optionally in excess, is then added at elevated temperature and the reaction mixture is maintained at that temperature for about from 2 to 4 hours. The mixture is cooled to room temperature and filtered, and the 4,5-diacyl-[1,4,5]-oxadiazepine is isolated from the filtrate by concentration by evaporation. That compound is then dissolved or suspended in a high-boiling alcohol. Hydrohalic acid, optionally in excess, is then passed into the solution or suspension at a temperature of about 50° C. The reaction mixture is then maintained at that temperature for a further 12 to 14 hours, degassed, cooled and filtered, and the residue is washed, yielding the hydrogen halide salt of the [1,4,5]-oxadiazepine.

The process according to the invention can be carried out continuously or batchwise (discontinuously), batchwise operation being preferred. Both the batchwise reaction procedure and the continuous reaction procedure are carried out especially in a stirred vessel or a stirred vessel cascade.

The process according to the invention has the following advantages over the processes of the prior art:
  it can be carried out on an industrial scale
  it can be carried out in a multi-purpose apparatus it yields both the intermediates and the end products in higher purity it yields both the intermediates and the end products in higher yields it is not necessary to isolate the intermediates it allows comparatively low reaction temperatures, especially in reaction step (1)

The [1,4,5]-oxadiazepine derivatives prepared according to the invention are used especially as intermediates in the preparation of herbicides of the tetrahydropyrazolodione type, which are described, for example, in WO 99/47525.

The following Examples further illustrate the invention.

EXAMPLE 1

Preparation of 4,5-diacetyl-[1,4,5]-oxadiazepine 10.6 g of finely pulverised 85% potassium hydroxide are introduced into a solution of 9.3 g of N,N'-diacetylhydrazine and 141 g of dimethyl sulfoxide in such a manner that a temperature of 33° C. is not exceeded. After heating to 80 to 85° C., 23 g of 2,2'-dichlorodiethyl ether are added dropwise to the reaction mixture over the course of 50 minutes. The resulting highly fluid suspension is maintained at 80 to 85° C. for 3 hours, then cooled to 20 to 25° C. and filtered, and the filtration residue is washed with dimethyl sulfoxide. 11.4 g (76.0%) of 4,5-diacetyl-[1,4,5]-oxadiazepine are obtained from the combined filtrates by concentration by evaporation.

EXAMPLE 2

Preparation of 4,5-diacetyl-[1,4,5]-oxadiazepine 105.6 g of finely pulverised potassium hydroxide are introduced into a solution of 92.9 g of N,N'-diacetylhydrazine and 1410 g of dimethyl sulfoxide. When the heat of reaction has died away, 229.9 g of 2,2'-dichlorodiethyl ether are added and then 221.1 g of finely ground potassium carbonate are introduced. The reaction mixture is heated to 70° C. and maintained at 70 to 75° C. for 2 hours, then cooled to 20 to 25° C. and filtered, and the filtration residue is washed with dimethyl sulfoxide. Concentration of the combined filtrates by evaporation yields an oil, to which 157 g of isopropanol are added. After cooling to −10° C., filtration is carried out and the crystalline residue is washed with isopropanol. After drying of the residue, 99.4 g (65.1%) of 4,5-diacetyl-[1,4,5]-oxadiazepine are obtained in a purity of 97.6%.

EXAMPLE 3

Preparation of [1,4,5]-oxadiazepine Hydrochloride 19.7 g of hydrogen chloride (anhydrous) are passed into a solution of 19.1 g of 4,5-diacetyl-[1,4,5]-oxadiazepine and 70 g of diethylene glycol over a period of 8 to 10 hours and the reaction mixture is then maintained at 43 to 45° C. for 10 to 12 hours. After the reaction suspension has been degassed at 40 to 45° C., filtration is carried out at a temperature of 10° C. and the residue is washed with cold methyl acetate. After drying of the residue, 13.2 g (85.0%) of [1,4,5]-oxadiazepine hydrochloride are obtained in a purity of 90.0% with approximately 8.5% diethylene glycol bound in the crystals.

EXAMPLES 4-8

Preparation of 4,5-diacetyl-[1,4,5]-oxadiazepine 39.6 g of potassium hydroxide powder 85% (0.6 mol) are introduced into a mixture of 35 g of diacetylhydrazine (0.3 mol) and 560 ml of solvent (see Table 1). When the heat of reaction has died away, 85.8 g of 2,2-dichlorodiethyl ether (0.6 mol) are added; the reaction mixture is heated to 80° C. and maintained at 80-90° C. for 5 hours. The mixture is then cooled to 20° C. and filtered, and the filtration residue is washed with the solvent. The yield is given by the content of title compound in the combined filtrate. It will be seen that the solvents used according to the invention (tests 4-7) give far better yields of 4,5-diacetyl-[1,4,5]-oxadiazepine than N,N-dimethylformamide, which is known from the above prior art (DMFA, comparison test 8).

TABLE 1

| Test No. | Solvent | [g] | [ml] | Yield [%] | Addition |
|---|---|---|---|---|---|
| 4 | 2-methyl-pyrrolidone | 578 | 560 | 39.1 | |
| 5 | dimethyl sulfoxide | 616 | 560 | 73.2 | |
| 6 | N,N-dimethyl-acetamide | 527.5 | 560 | 41.2 | |
| 7 | N,N-dimethyl-acetamide | 530 | 562.5 | 46.5 | Addition of 5 mol % benzyltriethyl-ammonium chloride as phase transfer catalyst |
| 8 | N,N-dimethyl-formamide | 531 | 560 | 15.2 | |

EXAMPLES 9-13

Preparation of 4,5-diacetyl-[1,4,5]-oxadiazepine

A mixture of 35 g of diacetylhydrazine (0.3 mol), 124.4 g or 165.8 g of ground potassium carbonate (0.9 or 1.2 mol, respectively), 85.8 g of 2,2-dichlorodiethyl ether (0.6 mol) and 560 ml of solvent (see Table 2) is heated to 125° C. and maintained at 125-130° C. or 80-90° C. (in the case of DMSO) for 5 hours. The mixture is then cooled to 20° C. and filtered, and the filtration residue is washed with the solvent. The yield is given by the content of title compound in the combined filtrate.

TABLE 2

| Test No. | Solvent | [g] | [ml] | Yield [%] | Amount of base [eq.] | Temp. [° C.] |
|---|---|---|---|---|---|---|
| 9 | N,N-dimethyl-acetamide | 527.5 | 560 | 63.0 | 3 | 125-130 |
| 10 | 2-methyl-pyrrolidone | 578 | 560 | 61.4 | 3 | 125-130 |
| 11 | sulfolane | 711 | 560 | 60.3 | 3 | 125-130 |
| 12 | dimethyl sulfoxide | 616 | 560 | 64.5 | 3 | 80-90 |
| 13 | dimethyl sulfoxide | 616 | 560 | 72.8 | 4 | 80-90 |

EXAMPLE 14

Preparation of 1,2-(phthalyl)diazo-5-oxacycloheptane 39.6 g of potassium hydroxide powder 85% (0.6 mol) are introduced into a mixture of 49.1 g of 2,3-dihydro-1,4-phthalazinedione (0.3 mol) and 616 g of dimethyl sulfoxide. When the heat of reaction has died away, 85.8 g of 2,2- dichlorodiethyl ether (0.6 mol) are added and the reaction mixture is heated to 80° C. and maintained at 80-90° C. for 5 hours. The mixture is then cooled to 20° C. and filtered, and the filtration residue is washed with dimethyl sulfoxide. The solvent is removed from the combined filtrates by distillation, and 100 g of n-pentanol are added to the residual oil, the product crystallising out. Filtration and washing of the filtration residue yields 22.5 g, or 25%, of the title compound.

EXAMPLE 15

Preparation of 4,5-diacetyl-[1,4,5]-oxadiazepine

A mixture of 11.6 g of diacetylhydrazine (0.1 mol), 29.0 g of ground potassium carbonate (0.21 mol), 31.5 g of 2,2-dimesyl diethyl ether (0.12 mol) and 177 g of dimethyl sulfoxide is heated to 80° C. and maintained at 80-85° C. for 6 hours. The mixture is then cooled to 20° C. and filtered, and the filtration residue is washed with 50 g of dimethyl sulfoxide. The filtrate is completely concentrated by evaporation, and 20 ml of water are added to the oily residue. Extraction three times with ethyl acetate, drying of the combined extracts over sodium sulfate, concentration by evaporation and crystallisation of the residue from n-pentanol yields 10.8 g, or 58.4%, of the title compound.

What is claimed is:

1. A process for the preparation of a 4,5-diacyl-[1,4,5]-oxadiazepine comprising: (1) reacting N,N'-diacylhydrazine with a 2,2'-disubstituted diethyl ether in a polar solvent in the presence of a base and at an elevated temperature to form the corresponding 4,5-diacyl-[1,4,5]-oxadiazepine and (2) optionally reacting the 4,5-diacyl-[1,4,5]-oxadiazepine with a hydrohalic acid in a polar solvent at an elevated temperature to form the corresponding [1,4,5]-oxadiazepine, wherein in reaction step (1) the solvent is selected from the group consisting of DMSO, sulfolane, NMP and DMA and wherein the base is selected from the group consisting of hydroxides, carbonates, alcoholates of alkali and alkaline earth metals, and mixtures thereof and in reaction step (2) the polar solvent is an alcohol having a boiling point above 100° C.

2. A process for preparing [1,4,5]-oxadiazepines, comprising:
(A) reacting a selected N,N'-diacylhydrazine with a selected 2,2'-disubstituted diethyl ether in the presence of a solvent to form a 4,5-diacyl-[1,4,5]-oxadiazepine, wherein said solvent is selected from the group consisting of DMSO, sulfolane, NMP, and DMA; and
(B) reacting said 4,5-diacyl-[1,4,5]-oxadiazepine with a selected hydrohalic acid to produce [1,4,5]-oxadiazepines.

3. A process according to claim 2 wherein said reaction between said N,N'-diacylhydrazine and said 2,2'-disubstituted diethyl ether occurs in the presence of a base.

4. A process according to claim 3 wherein said base is selected from the group consisting of hydroxides, carbonates, alcoholates of alkali and alkaline earth metals, and mixtures thereof.

5. A process according to claim 3 wherein said base is selected from the group consisting of potassium hydroxide, potassium carbonate, and a mixture thereof.

6. A process according to claim 2 wherein the step of reacting said 4,5-diacyl-[1,4,5]-oxadiazepine with a said hydrohalic acid occurs in the presence of an alcohol.

7. A process according to claim 6 wherein said alcohol is selected from the group consisting of n-butanol, n-pentanol, cyclohexanol, phenol, benzyl alcohol, glycol, diethylene glycol, glycerol and $C_1$-$C_4$alkoxy-$C_1$-$C_4$alcohols.

8. A process according to claim 2 wherein said hydrohalic acid is hydrogen chloride or hydrogen bromide.

9. A process according to claim 2 wherein said solvent is DMSO.

10. A process according to claim 2 wherein step (A) and step (B) occur at a temperature of between about 30° C. and 150° C.

11. A process according to claim 2 wherein the step of reacting said N,N'-diacylhydrazine with said 2,2'-disubstituted diethyl ether occurs at a temperature of between about 60° C. and 100° C.

12. A process according to claim 2 wherein the step of reacting said 4,5-diacyl-[1,4,5]-oxadiazepine with said hydrohalic acid occurs at a temperature of between about 30° C. to 60° C.

13. A process according to claim 2 wherein potassium iodide, a crown ether, and a phase transfer catalyst are added during the step of reacting said N,N'-diacylhydrazine with a selected 2,2'-disubstituted diethyl ether.

14. A process according to claim 2 wherein said process is batchwise.

* * * * *

UNITED STATES PATENT AND TRADEMARK OFFICE
CERTIFICATE OF CORRECTION

PATENT NO. : 7,598,376 B2 Page 1 of 1
APPLICATION NO. : 10/498865
DATED : October 6, 2009
INVENTOR(S) : Jau et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 202 days.

Signed and Sealed this

Twenty-eighth Day of September, 2010

David J. Kappos
*Director of the United States Patent and Trademark Office*